(12) United States Patent
Tian et al.

(10) Patent No.: US 9,557,171 B2
(45) Date of Patent: *Jan. 31, 2017

(54) RECIPROCATING OCEAN MICROSTRUCTURE PROFILER

(71) Applicant: Ocean University of China, Qingdao (CN)

(72) Inventors: Jiwei Tian, Qingdao (CN); Dalei Song, Qingdao (CN); Wei Zhao, Qiangdao (CN); Ming Xu, Qingdao (CN); Qingxuan Yang, Qiangdao (CN)

(73) Assignee: OCEAN UNIVERSITY OF CHINA, Qingdao (CN)

( * ) Notice: Subject to any disclaimer, the term of this patent is extended or adjusted under 35 U.S.C. 154(b) by 120 days.

This patent is subject to a terminal disclaimer.

(21) Appl. No.: 14/567,112

(22) Filed: Dec. 11, 2014

(65) Prior Publication Data
US 2015/0354957 A1 Dec. 10, 2015

(30) Foreign Application Priority Data

Jun. 9, 2014 (CN) .......................... 2014 1 0252441

(51) Int. Cl.
| | | |
|---|---|---|
| *G01C 13/00* | (2006.01) | |
| *B63B 22/20* | (2006.01) | |
| *G01N 33/18* | (2006.01) | |
| *B63B 22/00* | (2006.01) | |

(52) U.S. Cl.
CPC .............. *G01C 13/00* (2013.01); *B63B 22/00* (2013.01); *G01N 33/1886* (2013.01); *B63B 2022/006* (2013.01); *B63B 2211/02* (2013.01)

(58) Field of Classification Search
CPC .... G01C 13/00; G01N 33/18; G01N 33/1886; B63B 22/00; B63B 22/18; B63B 22/20; B63B 2211/02; B63B 2022/006
See application file for complete search history.

(56) References Cited

U.S. PATENT DOCUMENTS

| | | | | |
|---|---|---|---|---|
| 4,924,698 A | * | 5/1990 | Echert ...................... | B63B 22/18 441/33 |
| 5,644,077 A | * | 7/1997 | Fowler ...................... | B63B 3/04 73/170.29 |
| 5,869,756 A | * | 2/1999 | Doherty .................. | B63B 22/18 405/188 |

(Continued)

*Primary Examiner* — Nguyen Ha
(74) *Attorney, Agent, or Firm* — Buchanan Ingersoll & Rooney PC

(57) ABSTRACT

A reciprocating ocean microstructure profiler includes a first profiler subunit, a second profiler subunit and a central stand. The first profiler subunit is provided with the first buoyancy drive part and the first observation part; and the second profiler subunit is provided with the second buoyancy drive part and the second observation part. Both the first and second buoyancy drive parts are installed with a floating compartment, a drive compartment and a pressure housing each. A top oil bladder is provided in the floating compartment and a bottom oil bladder in the pressure housing. A drive pump assembly and a solenoid valve are installed in the drive compartment. The first and second observation parts are electrically connected to a controller each and each controller is electrically connected to a drive pump assembly and a solenoid valve.

11 Claims, 5 Drawing Sheets

(56) References Cited

U.S. PATENT DOCUMENTS

| | | | |
|---|---|---|---|
| 2008/0087209 A1* | 4/2008 | Yoshida | B63B 22/20 114/333 |
| 2012/0204775 A1* | 8/2012 | Watanabe | B63G 8/24 114/56.1 |
| 2015/0354956 A1* | 12/2015 | Tian | G01C 13/00 73/170.29 |

* cited by examiner

RECIPROCATING OCEAN MICROSTRUCTURE PROFILER

CROSS-REFERENCE TO RELATED APPLICATIONS

The present application claims the priority of CN 201410252441.1, filed in China on Jun. 9, 2014. The present application incorporates by reference the entirety of CN 201410252441.1 and the application filed in the U.S. on even date herewith by the same inventors titled METHOD FOR THE MEASUREMENT OF TURBULENCE BY USING RECIPROCATING OCEAN MICROSTRUCTURE PROFILER.

TECHNICAL FIELD

The present invention belongs to technical field of the ocean explorer and relates to a device capable of providing all-round ocean exploration, in particular to a reciprocating ocean microstructure profiler.

BACKGROUND

People's understanding and exploration of the ocean can be dated back to the $3^{rd}$ century BC. Later, pure commercial and expedition voyage, voyage involving scientific meanings and pure scientific investigation based on modern technology follow. Oceanography is an observation-based science and every leap in the process of cognition on the ocean is based on the advent of a new observation method and measuring device. Looking back to the marine observation history, the invention of the acoustic Doppler current profiler enabled people to understand the large-scale circulation structure in the globe; the appearance of the conductivity-temperature-depth (CTD) profiler enabled the people to ascertain the large-scale water mass formation and transformation in the entire ocean, the launch of various satellite altimeters enabled the people to make preliminary cognition on meso-scale and small-scale processes in the ocean such as spatial structure and time evolution of meso-scale eddies and internal waves.

Great process has been made in the meso- and large-scale process concerning the research of oceanography but the scientific research of micro-scale has just started. In recently years, the shear, temperature and conductivity probes for high-frequency sampling have been successfully developed, which draws the curtain of the research on ocean micro-scale process. Currently, there are two methods in the measurement of ocean microstructure, namely mooring point measurement method and shipboard vertical profile measurement method. The former only conducts measurement at a specific depth of a fixed position in the ocean and it could contribute to better time-series observation but fails to obtain the characteristics of the vertical structure of the ocean. As for the latter, an oceanographic vessel is used to measure the ocean microstructure from the ocean surface to a specific depth; however, it is impossible to obtain the time variation characteristics of the ocean microstructure and the measurement may be subject to the limitation of some unfavorable factors including ocean conditions and complex site operation, etc. With respect to the research of ocean microstructure, time variation and spatial structure represents two important parameters for describing the characters of the research. Therefore, the ocean micro-scale structure observation device aiming to obtain the changes both in the spatial structure in vertical and time variation is to be urgently developed. In the description or research of ocean microstructure, turbulent kinetic energy dissipation rate is an important physical variable. Therefore, the direct and accurate measurement on the turbulent kinetic energy dissipation rate is of great significance on the transfer and dissipation of the turbulent energy. In recent years, the shear probe for high-frequency sampling is able to accurately measure the turbulence kinetic energy dissipation rate but its application is based on either mooring point measurement method or shipboard vertical profile measurement method and fails to realize the integration of both two methods. It can be seen that the shear probe for high-frequency sampling plays an important role in breaking through the bottleneck of ocean microstructure observation, making the observation methods and platform innovated and enabling the organic integration of both platforms above.

SUMMARY OF THE INVENTION

According to the problems in the prior art above, the objective of the present invention is to propose a reciprocating ocean microstructure profiler used for long-term continuous profile observation of turbulent kinetic energy dissipation rate by vertically and permanently laying steel cable in the ocean, adopting symmetric stable structure and applying a shear probe for direct detection.

The objective of the present invention are realized by the following technical scheme: A reciprocating ocean microstructure profiler, characterized in that said profiler comprises the first profiler subunit, the second profiler subunit and a central stand, with both profiler subunits fixed onto the central stand on the left and right sides respectively. A steel cable penetration hole for connecting the steel cable and the central stand is provided on the central axis of the central stand. The steel cable travels through the central stand through the steel cable penetration hole. The central stand can slide upward and downward along the steel cable. An upper limit part and a lower limit part for limiting the sliding distance of the central stand are provided on the steel cable. Said first profiler subunit is provided with the first buoyancy drive part and the first observation part in proper sequence from top to bottom, with said first buoyancy drive part being provided with a floating compartment, a drive compartment and a pressure housing in proper sequence from top to bottom; an top oil bladder is provided in the floating compartment and a bottom oil bladder in the pressure housing; a drive pump assembly and a solenoid valve are provided in the drive compartment; said drive pump assembly is communicated to both upper and bottom oil bladders through an oil return line; said first observation part is electrically connected to a controller, with said controller being electrically connected to the drive pump assembly and the solenoid valve. Said second profiler subunit is provided with the second buoyancy drive part and the second observation part in proper sequence from top to bottom, with said second buoyancy drive part being provided with a floating compartment, a drive compartment and a pressure housing in proper sequence from top to bottom; an top oil bladder is provided in the floating compartment and a bottom oil bladder in the pressure housing; a drive pump assembly and a solenoid valve are provided in the drive compartment; said drive pump assembly is communicated to both upper and bottom oil bladders through an oil return line; said second observation part is electrically connected to a controller, with said controller being electrically connected to the drive pump assembly and the solenoid valve.

In the present reciprocating ocean microstructure profiler, steel cable may travel through any sea area and the whole profiler ascends and descends within a range of water depth of 800 to 2,500 m along the steel cable. A control system is used to control the bottom oil bladder of the first and second profiler subunits in feeding oil to the top oil bladder so as to increase the volume of the top oil bladder, reduce the density of the floating compartment and drive the profiler to slide upward along the steel cable. When the top oil bladder is controlled to return oil to the bottom oil bladder, the volume of the top oil bladder will become smaller so as to increase the density of the floating compartment and cause the profiler to slide downward along the steel cable. During the process of the ascending and descending of the reciprocating ocean microstructure profiler, the continuous profile measurement of ocean microstructure including ocean temperature, salinity, pressure as well as profile turbulence is realized.

In the reciprocating ocean microstructure profiler aforementioned, said first observation part includes a temperature probe, a shear probe and a depth sensor on the bottom of the first profiler subunit; said second observation part includes a conductivity-temperature-depth (CTD) profiler, a current meter and a gesture sensor; and said shear probe is used to measure the fluctuating velocity of current. In the reciprocating ocean microstructure profiler aforementioned, said controller is provided with a main control module and a data acquisition module. Said main control module includes a plurality of information receiving ports. Said temperature probe includes an ordinary temperature detection module and a fast temperature detection module. Said ordinary temperature detection module includes a common temperature sensor, a temperature measuring bridge and a preamplifier in series; and said fast temperature detection module includes a fast temperature sensor, a linear amplifier and a frequency compensator in series, with the frequency compensator branch being connected to a pre-emphasis circuit or an adaptive coupling linear amplifier. Said shear probe has a shear detection module. Said shear detection module includes a shear sensor, a high-pass filter preamplifier and a low-pass filter preamplifier. Said depth sensor has a pressure detection module. Said pressure detection module includes a depth sensor and a signal conditioner in series. Said ordinary temperature detection module, fast temperature detection module, shear detection module and pressure detection module are connected to the information receiving ports of the main control module through the data acquisition module respectively.

In the reciprocating ocean microstructure profiler aforementioned, said current meter comprises a current sensing module; said CTD profiler comprises a thermohaline sensing module; said gesture sensor comprises a gesture sensor; and said current sensing module, thermohaline sensing module as well as gesture sensor are connected to the information acquisition ports of the main control module.

In the reciprocating ocean microstructure profiler aforementioned, said controller is also provided with a buoyancy drive control module, a clock module, a storage module, a PC (personal computer) and a power module; said main module communicates with said clock module, storage module, PC (personal computer) and buoyancy drive control module; said main control module is also connected to the power module and said power module is connected to a battery.

In the reciprocating ocean microstructure profiler aforementioned, said drive pump assembly include a motor and a HP pump; said HP pump is connected to the oil outlet line in series; said motor is connected to the HP pump through the speed reducer driver; and said controller is electrically connected to the motor. Start the motor and provide power source to the HP pump through the speed reducer so as to pump the oil from the bottom oil bladder to the top oil bladder.

In the reciprocating ocean microstructure profiler aforementioned, said electromagnetic valve comprises two circuits connected in parallel, with one circuit being provided with a check valve and the other circuit provided with a flow control valve. The check valve is used to prevent the hydraulic oil flowing from the bottom oil bladder to the top oil bladder via the oil return line; the oil quantity is controlled by adjusting the open degree of the flow control valve and the descent rate of the profiler is further controlled.

In the reciprocating ocean microstructure profiler aforementioned, the top of said first and second profiler subunits are provided with a brush damper each and said brush damper comprises a plurality of brush blades evenly distributed in a radial pattern. When the first or second profiler subunit ascends or descends in the ocean, the brush damper can play the role of friction reduction.

In the reciprocating ocean microstructure profiler aforementioned, said central stand includes a cylindrical frame in the middle part; both sides of said cylindrical frame are permanently and symmetrically provided with a plurality of support sleeves; said first and second profiler subunits are fixed in the support sleeves at the same side and a plurality of steel cable penetration holes are provided and arranged in the length direction of the cylindrical frame, the circumferential pulleys are provided at the upper and lower ends of each steel cable penetration hole and the steel cable passes through the steel cable penetration holes and connected with the circumferential pulleys in a sliding fashion.

In the reciprocating ocean microstructure profiler aforementioned, limit disks are provided in both upper and lower positions; the steel wire is fixed at the central holes of the limit disks; and said steel cable is provided with plastic surface. The steel cable is sheathed with a plastic surface layer that is favorable for sliding and contact and protects the steel cable against erosion and aging.

The reciprocating ocean microstructure profiler aforementioned, buffer springs are provided on the bottom of said central stand and used to realize the elastic buffer impact in combination with the lower limit position. Under the elastic buffer function of the buffer spring, impact is reduced so as to avoid damages when the profiler reaches the lower limit position to avoid damages.

Compared with the prior art, this detection method of the reciprocating ocean microstructure profiler is provided with a steel cable that can be located in and penetrate any sea area profile, eliminating the need for labor every time, so that the equipment automatically provides long-term continuous profile measurement at the fixed area along the steel cable; it adopts integrated symmetrical structure with the center of gravity located below the center of buoyancy, improving the center stability, thus ensuring high stability of the entire system on the hydrodynamic layout; it can achieve the changeover between positive buoyancy and negative buoyancy, steady reciprocating ascending and descending operations and accurate positioning during ascending and descending operations by utilizing the position change of hydraulic oil due to discharge and return; it integrates the CTD profiler, current meter, temperature probe, shear probe, depth sensor and gesture sensor, thus achieving all-round ocean microstructure profile measurement, wherein the turbulence kinetic energy dissipation rate can be directly derived from the fluctuating velocity measured by the shear probe so as to achieve long-term continuous profile observation on the turbulence kinetic energy dissipation rate.

In the figures above, 1. steel cable; 2. limit disc; 3. central stand; 4. buffer spring; 5. brush damper; 6. floating compartment; 7. top oil bladder; 8. drive compartment; 9. motor; 10. HP pump; 11. solenoid valve; 12. pressure housing; 13. bottom oil bladder; 14. CTD profiler; 15. current meter; 16. temperature probe; 17. shear probe.

SPECIFIC EMBODIMENTS

Here are the specific embodiments of the present invention and the technical scheme of the present invention is further described in reference to the drawings, but the present invention is not limited to these embodiments.

Figure 1:
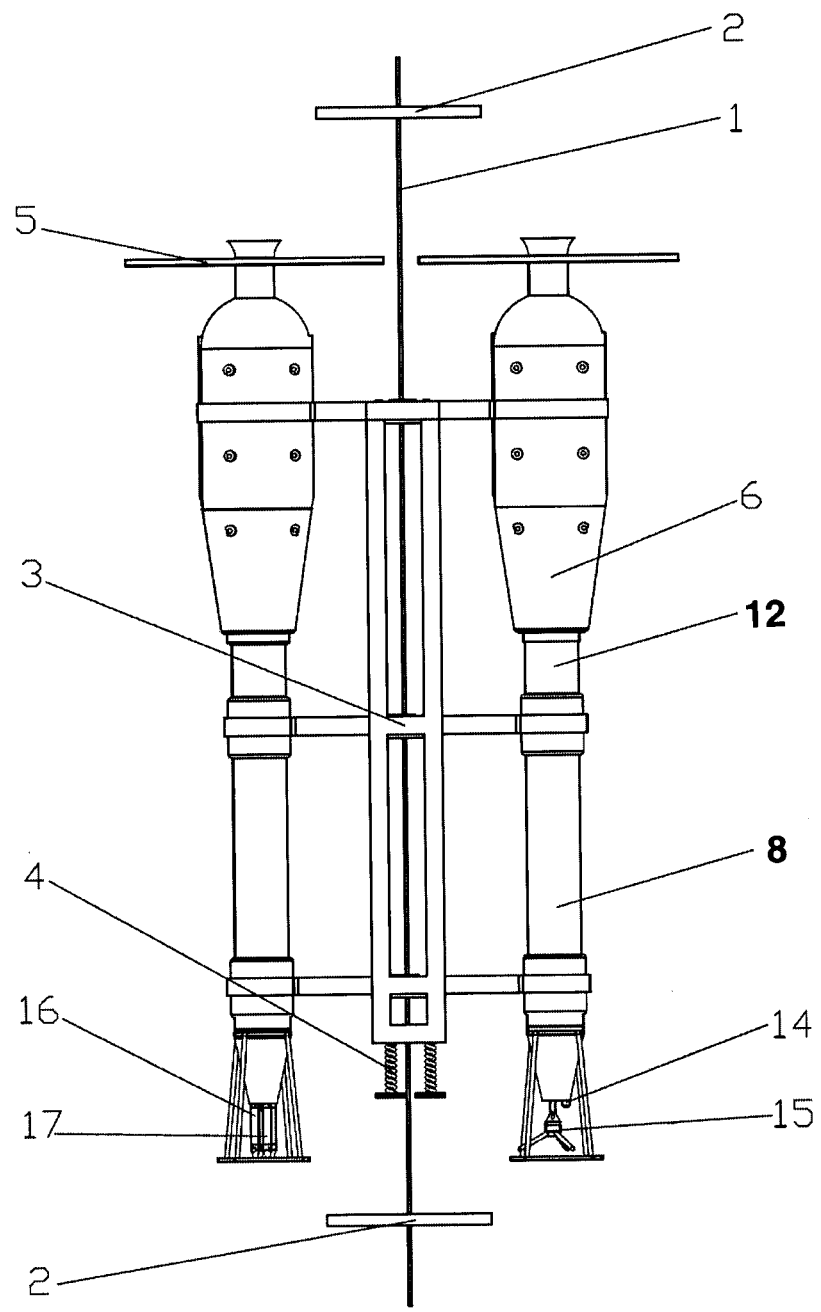
FIG. 1 illustrates an overall structure sketch for the present reciprocating ocean microstructure profiler.
Figure 2:
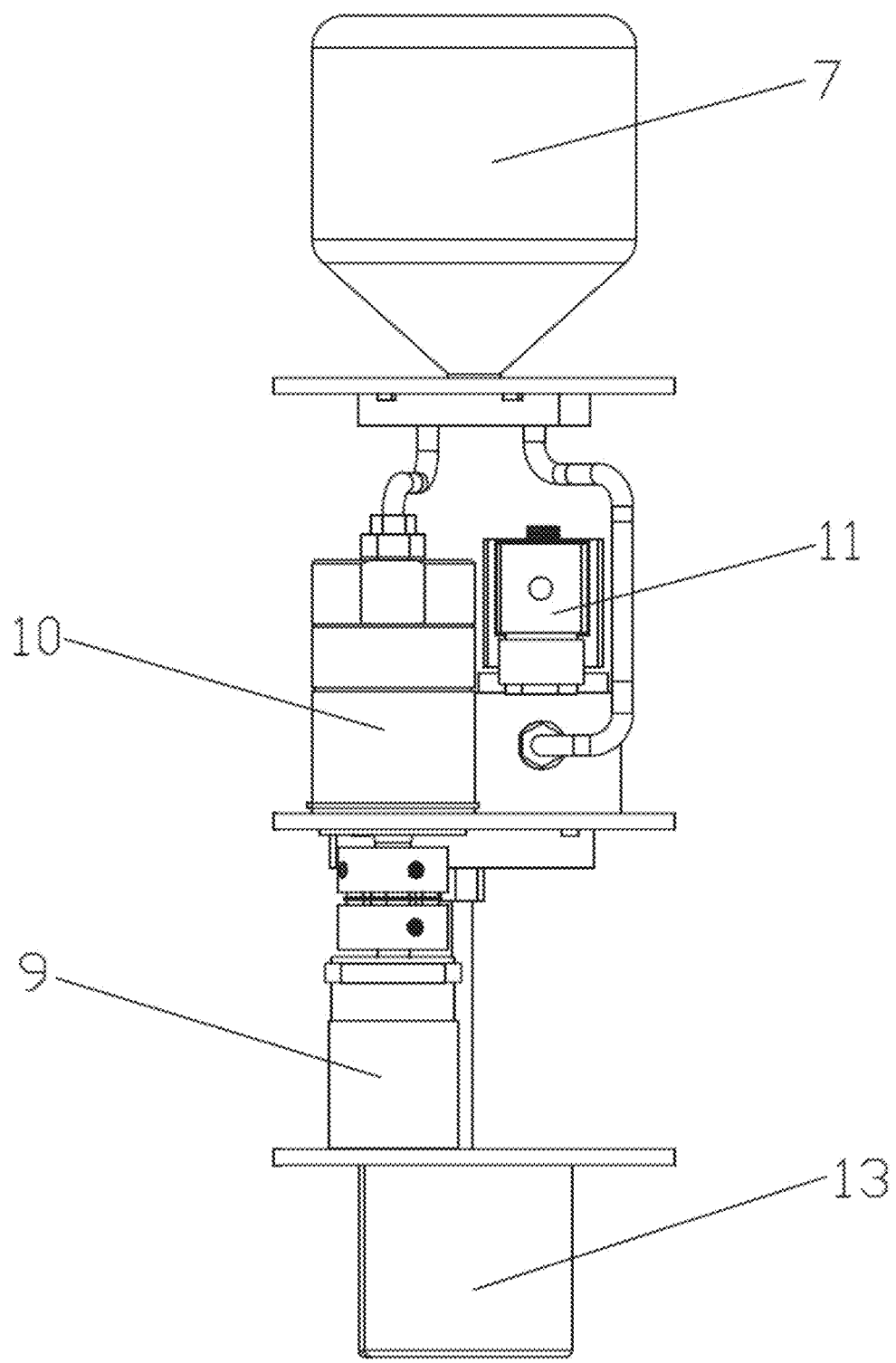
FIG. 2 illustrates a structure sketch for the buoyancy drive part of the present reciprocating ocean microstructure profiler.
Figure 3:
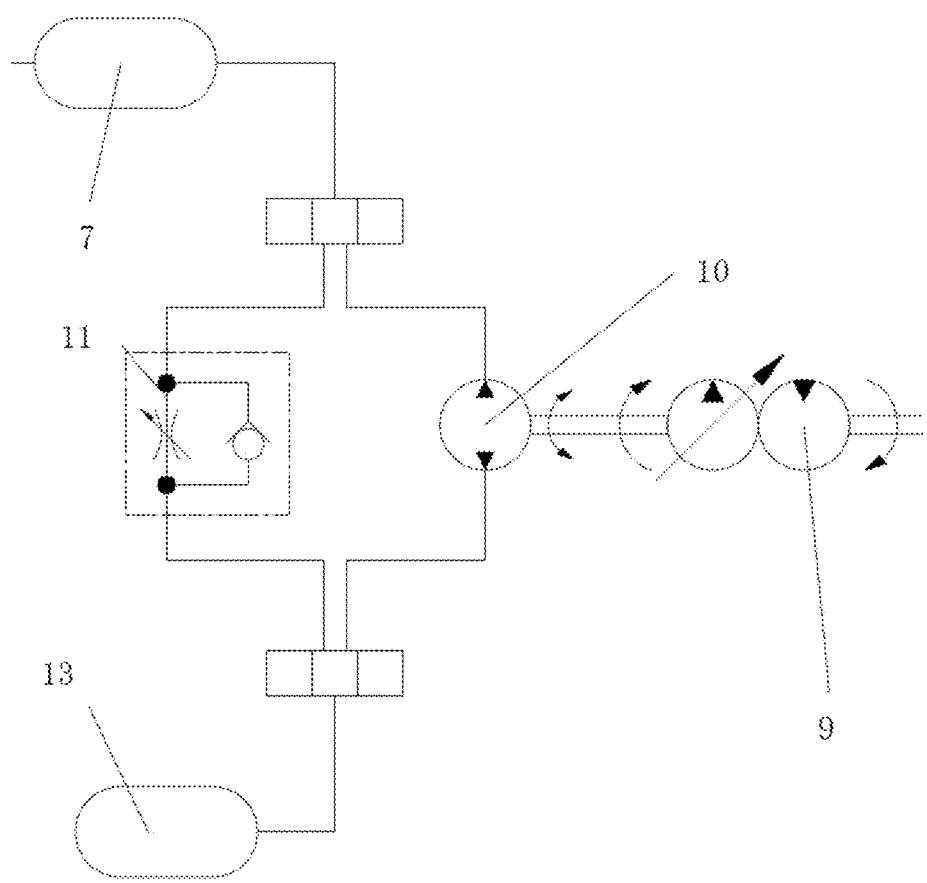
FIG. 3 illustrates a schematic diagram for the buoyancy drive part of the present reciprocating ocean microstructure profiler.

As shown in FIGS. 1, 2 & 3, the present reciprocating ocean microstructure profiler comprises the first profiler subunit, the second profiler subunit and a central stand 3, wherein these two profiler subunits are secured to the central stand 3, a steel cable penetration hole for connecting the steel cable 1 to the central stand 3 is provided at the central axis of the central stand 3 and the steel cable 1 longitudinally penetrates the central stand 3 via the steel cable penetration hole, the central stand 3 can slide up and down along the steel cable 1 and the steel cable 1 can longitudinally penetrate in any sea area.

The steel cable 1 is sheathed with a plastic surface layer that is favorable for sliding and contact and protects the steel cable 1 against erosion and aging. The upper limit part and lower limit part are provided at the upper and lower limit positions of the steel cable 1 to limit the sliding distance of the central stand 3. Both the upper limit part and lower limit part are limit discs 2 and the steel cable is secured at the center holes of the limit discs 2.

The central stand 3 is provided with a cylindrical frame located at the center, several support sleeves are secured to both sides of the cylindrical frame, and at each side, the upper, middle and lower support sleeves are provided at the upper, middle and lower positions of the first profiler subunit or the second profiler subunit respectively. Several steel cable penetration holes are provided and arranged in the length direction of the cylindrical frame, the circumferential pulleys are provided at the upper and lower ends of each steel cable penetration hole and the steel cable passes through the steel cable penetration holes and connected with the circumferential pulleys in a sliding fashion.

A buffer spring 4 located at the bottom of the central stand 3 will receive elastic buffer impact with the limit disc 2 at the bottom when the central stand 3 descends to the lower limit position. Under the elastic buffer function of the buffer spring 4, impact is reduced so as to avoid damages when the profiler reaches the lower limit position to avoid damages.

The brush dampers 5 are located at the tops of the first profiler subunit and the second profiler subunit and provided with several brush blades that are arranged uniformly in a radial form. When the whole profiler makes ascending and descending motions in the sea water, the brush damper 5 can reduce resistance.

The first profiler subunit is provided with the first buoyancy drive part and the first observation part from top to down, the first buoyancy drive part is provided with a floating compartment 6 holding a top oil bladder 7, a drive compartment 8 holding a bottom oil bladder 13, and a pressure housing 12 holding a drive pump assembly and a solenoid valve 11. An oil outlet line and an oil return line are provided in the drive compartment 8 to form a circulation loop that connects the top oil bladder 7 and the bottom oil bladder 13. The drive pump assembly comprises a motor 9 and HP pump 10, wherein the HP pump 10 is connected in series to the oil outlet line and the motor 9 drives and is connected to the HP pump 10 via the speed reducer, through which, the started-up motor 9 powers the HP pump 10 so as to pump oil from the bottom oil bladder 13 to the top oil bladder 7. The solenoid valve 11 is connected in series to the oil return line and provided with two lines in parallel, one line is provided with a check valve that prevents hydraulic oil from running from the bottom oil bladder 13 to the top oil bladder 7 via the oil return line and the other is provided with a flow control valve that controls the openness of the valve through controlling the flow to control the oil return flow so as to control the descent rate of the profiler. The first observation part is electrically connected to the controller which is electrically connected to the motor 9 in the drive pump assembly and the solenoid valve 11.

The second profiler subunit is provided with the second buoyancy drive part and the second observation part from top to down, the second buoyancy drive part is provided with a floating compartment 6 holding a top oil bladder 7, a drive compartment 8 holding a bottom oil bladder 13, and a pressure housing 12 holding a drive pump assembly and a solenoid valve 11. An oil outlet line and an oil return line are provided in the drive compartment 8 to form a circulation loop that connects the top oil bladder 7 and the bottom oil bladder 13. The drive pump assembly comprises a motor 9 and HP pump 10, wherein the HP pump 10 is connected in series to the oil outlet line and the motor 9 drives and is connected to the HP pump 10 via the speed reducer, through which, the started-up motor 9 powers the HP pump 10 so as to pump oil from the bottom oil bladder 13 to the top oil bladder 7. The solenoid valve 11 is connected in series to the oil return line and provided with two lines in parallel, one line is provided with a check valve that prevents hydraulic oil from running from the bottom oil bladder 13 to the top oil bladder 7 via the oil return line and the other is provided with a flow control valve that controls the openness of the valve through controlling the flow to control the oil return flow so as to control the descent rate of the profiler. The second observation part is electrically connected to the controller which is electrically connected to the motor 9 in the drive pump assembly and the solenoid valve 11.

The first observation part comprises the temperature probe 16, shear probe 17 and depth sensor located at the bottom of the first profiler subunit and the second observation part comprises the CTD profiler 14, current meter 15 and gesture sensor located at the bottom of the second observation part, wherein the turbulence kinetic energy dissipation rate can be directly derived from the fluctuating velocity of the current measured by the shear probe 17. All detecting devices in the first observation part and the second observation part are connected via circuits to the controller where a battery and a turbulence detection circuit that detects and analyzes all detection information are provided.

Figure 4:
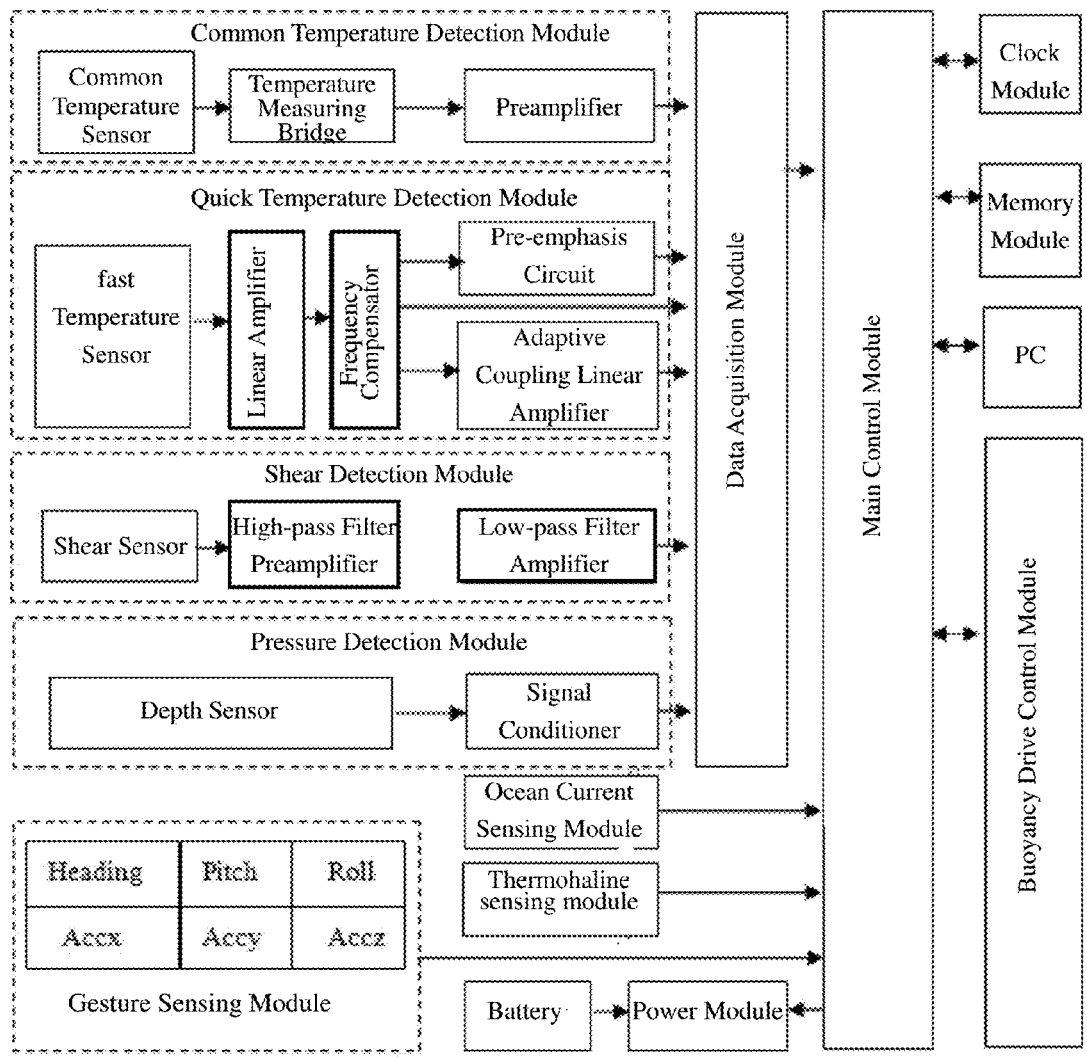
FIG. 4 illustrates a schematic diagram for the internal module structure of the controller in the present reciprocating ocean microstructure profiler.
Figure 5:
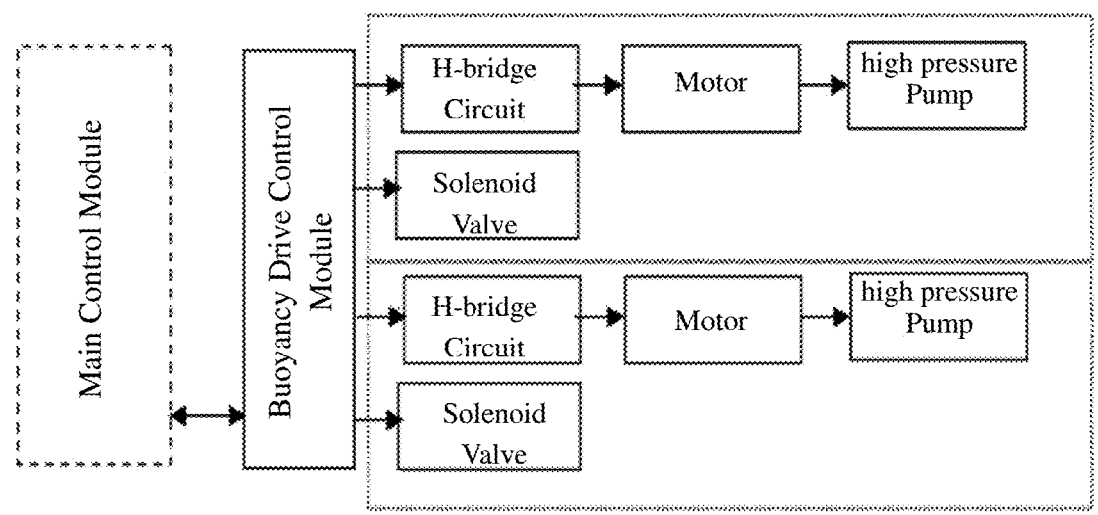
FIG. 5 illustrates a block diagram for the buoyancy drive part of the present reciprocating ocean microstructure profiler.

As shown in FIG. 4, the controller holds a main control module with several information receiving ports and a data acquisition module. The temperature probe 16 is provided with a common temperature detection module comprising the common temperature sensor, temperature measuring bridge and preamplifier that are connected in series and a fast temperature detection module comprising the fast temperature sensor, linear amplifier and frequency compensator that are connected in series and the pre-emphasis circuit and adaptive coupling linear amplifier that are connected as branches with the frequency compensator; the shear probe 17 is provided with a shear detection module comprising the shear sensor, high-pass filter preamplifier and low-pass filter amplifier that are connected in series; the depth sensor is provided with a pressure detection module comprising the depth sensor and signal conditioner that are connected in series. The common temperature detection module, fast temperature detection module, shear detection module and pressure detection module are connected to the information receiving ports of the main control module via the data acquisition module. The current meter 15 is provided with a current sensing module, the CTD profiler 14 is provided with a thermohaline sensing module, the gesture sensor is provided with a gesture sensing module and these three modules are connected to the information receiving ports of the main control module respectively.

The controller also holds a buoyancy drive control module, clock module, memory module, PC (personal computer) and power module. The main control module communicates mutually with the clock module, memory module, PC (personal computer) and buoyancy drive control module and is connected with the power module which is connected with a battery.

For the reciprocating ocean microstructure profiler, the profiler makes ascending and descending motions in the water depth range of 800 m to 2500 m along the steel cable; its platform moves at a speed of 0.2 m/s~0.3 m/s; its sampling frequency may be set to maximum value 1,024 Hz; its controller has a memory capacitance not less than 8 G.

In order to ensure the stable gesture of the profiler in the water, the center of gravity is designed to be located below the center of buoyancy, thus improving the center stability; furthermore, a structure that is fully symmetrical in appearance at the left and right sides is adopted to achieve adjustment of the center of gravity so that the center of buoyancy at both sides are identical and the center of gravity at both sides are also the same, ensuring the center of buoyancy and the center of gravity are on the geometrical axis of the profiler, thus ensuring high stability of the entire system on the hydrodynamic layout.

The ocean water pressure may cause the compression of the profiler volume and affects the static buoyancy of profiler in water. Also ocean water temperature may influence water density and the static buoyancy of profiler in water while a little change in the static buoyancy may cause the change in the speed of the profiler. Thus, it is necessary to measure the statics characteristics of the profiler under different water pressure and temperature so as to realize effective control on the movement of the profiler by using control algorithms. These tests will make determination in a visual temperature-regulating pressure tank.

1. Determination of Kinetic Parameters

Water resistance is a factor of influencing the movement of the profiler. According to the formula $F_{water\ resistance} = \frac{1}{2}\rho v^2 S C_D$, the inflow area S and drag coefficient CD needs to be measured. A six-dimensional force sensor is applied to determine the water resistance along the flow under different flow rates and estimate relevant parameters.

2. Optimized Design of Oil Bladder

As described above, one of the key technical indicators for the reciprocating ocean microstructure profiler is the moving speed of the platform. As a moving platform with buoyancy drive as power, the design of oil bag is one of the key issues met in design. Normally, a streamline cylinder has an axial drag coefficient of 0.15 to 0.2. As an initial design, the maximum value of 0.2 may be taken. Take the design speed of 0.5 m/s and kinetic head P0=0.5×1024×0.5×0.5=128 kg/m².

Characteristic area: S=3.14159×0.08×0.08=0.020 m².

Net force: F=P0×S×Cd=0.51 kg.

Oil quantity required: 2×0.51=1.02 kg.

As the speed during the ascending phase could be less than 0.5 m/s, the initially designed oil tank volume of 1 L can satisfy the kinetic demand of platform.

3. Large-Depth Buoyancy Drive and Control Technique

It is required that the buoyancy drive part should be able to work normally under the maximum operating depth of 4,000 m and have a regulating capacity of ±0.5–±1 L. In the present reciprocating ocean microstructure profiler, a control system is used to control the bottom oil bladder 13 of the first and second profiler subunits in feeding oil to the top oil bladder 7 so as to increase the volume of the top oil bladder 7, reduce the density of the floating compartment 6 and drive the profiler to slide upward along the steel cable 1. When the top oil bladder 7 is controlled to return oil to the bottom oil bladder 13, the volume of the top oil bladder 7 will become smaller so as to increase the density of the floating compartment 6 and cause the profiler to slide downward along the steel cable 1. The flow of hydraulic oil between the bottom oil bladder 13 and the top oil bladder 7 enables the conversion between positive and negative buoyancy and realize the ascending and descending of the reciprocating observation platform.

During the process of descending and ascending process of the present reciprocating ocean microstructure profiler, the CTD profiler 14, current meter 15, temperature probe 16, shear probe 17, depth sensor, gesture sensor and other detection devices transmit the detection information to the controller, which further sort out and analyze detection information and make a continuous profile measurement of ocean microstructure including ocean temperature, salinity, pressure and profile turbulence, etc. The shear probe 17 is used to directly calculate the turbulence kinetic energy dissipation rate and conduct a long-term continuous profile observation of the turbulence kinetic energy dissipation rate. Also, the controller synchronously transmits the drive command to the buoyancy drive control module which will control the operation of the motor 9 and solenoid valve 11 according to the drive command. The specific embodiments described herein only explain the spirit of the present invention as examples. The technologists in the technical field of the present invention may make various modifications to or similar replacements for the specific embodiments described herein but such modifications or replacements shall not deviate from the spirit of the present invention or exceed the scope defined in the attached claims.

Although following terms are used many times in the document: steel cable 1; limit disc 2; central stand 3; buffer spring 4; brush damper 5; floating compartment 6; top oil bladder 7; drive compartment 8; motor 9; HP pump 10; solenoid valve 11; pressure housing 12; bottom oil bladder 13; CTD profiler 14; current meter 15; temperature probe 16; shear probe 17 and so on, the possibility of using other terms is not eliminated. The foregoing terms are used only for describing and explaining the essence of the present invention more conveniently; construing them as any additional restriction conflicts with the spirit of the present invention.

What is claimed is:

1. A reciprocating ocean microstructure profiler, comprising:
    a first profiler subunit,
    a second profiler subunit, and
    a central stand having a central axis,
    a cable,
    a controller,
    wherein the first and second profiler subunits are secured to opposite sides of the central stand, respectively,
    a cable penetration hole for connecting the cable to the central stand is provided at the central axis of the central stand to enable the cable to longitudinally penetrate the central stand via the cable penetration hole, and the central stand is configured to slide up and down along the cable,
    an upper limit part and a lower limit part are provided on the cable to limit the sliding distance of the central stand,
    the first profiler subunit is provided with a first buoyancy drive part and a first observation part,
    the first buoyancy drive part is configured to perform ascending and descending operations of the profiler, and is provided with a first floating compartment holding a first top oil bladder, a first drive compartment holding a first bottom oil bladder, and a first pressure compartment holding a first drive pump assembly and a first solenoid valve,
    the first drive pump assembly connects the first top oil bladder to the first bottom oil bladder via a first oil outlet line,
    the first solenoid valve connects the first top oil bladder to the first bottom oil bladder via a first oil return line,
    the first observation part is electrically connected to the controller, which is electrically connected to the first drive pump assembly and the first solenoid valve,
    the second profiler subunit is provided with a second buoyancy drive part and a second observation part,
    the second buoyancy drive part is configured to perform ascending and descending operations of the profiler, and is provided with a second floating compartment holding a second top oil bladder, a second drive compartment holding a second bottom oil bladder, and a second pressure compartment holding a second drive pump assembly and a second solenoid valve,
    the second drive pump assembly connects the second top oil bladder to the second bottom oil bladder via a second oil outlet line,
    the second solenoid valve connects the second top oil bladder to the second bottom oil bladder via a second oil return line,
    the second observation part is electrically connected to the controller which is electrically connected to the second drive pump assembly and the second solenoid valve.

2. The reciprocating ocean microstructure profiler of claim 1,
    wherein the first observation part includes:
    a temperature probe having a common temperature detection module and a fast temperature detection module,
    a shear probe having a shear detection module for detecting the high-frequency fluctuating velocity of a current, wherein a turbulent kinetic energy dissipation rate is directly derived from a shear value of high-frequency fluctuating velocity, and
    a depth probe having a pressure detection module for measuring a depth of the profiler in water is measured by the pressure detection module located in the depth probe, thus obtaining the descent or ascent rate so as to calculate the turbulent kinetic energy dissipation rate,
    the second observation part includes:
    a current meter having a current sensing module to measure temperature, conductivity and pressure data, and
    a thermohaline sensing module located in a conductivity-temperature-depth (CTD) profiler,
    wherein the controller is configured to control ascending and descending operations of the profiler by controlling transfer of hydraulic oil from the first and second bottom oil bladders to the first and second top oil bladders, respectively,
    and the controller is also configured to generate a go to sleep mode command when each detecting device reaches or is close to its predefined lower limit position so as to wait for the next startup signal.

3. The reciprocating ocean microstructure profiler of claim 2, wherein said controller is provided with a main control module and a data acquisition module, said main control module includes a plurality of information receiving ports, said temperature probe includes an ordinary temperature detection module and a fast temperature detection module, said ordinary temperature detection module includes a common temperature sensor, a temperature measuring bridge and a preamplifier in series; and said fast temperature detection module includes a fast temperature sensor, a linear amplifier and a frequency compensator in series, with the frequency compensator branch being connected to a pre-emphasis circuit or an adaptive coupling linear amplifier, said shear probe has a shear detection module, said shear detection module includes a shear sensor, a high-pass filter preamplifier and a low-pass filter preamplifier, said depth sensor has a pressure detection module, said pressure detection module includes a depth sensor and a signal conditioner in series, said ordinary temperature detection module, fast temperature detection module, shear detection module and pressure detection module are connected to the information receiving ports of the main control module through the data acquisition module respectively.

4. The reciprocating ocean microstructure profiler of claim 1, wherein said first observation part includes a temperature probe, a shear probe and a depth sensor on the bottom of the first profiler subunit; said second observation part includes a conductivity-temperature-depth (CTD) profiler, a current meter and a gesture sensor; and said shear probe is configured to measure the fluctuating velocity of current in high frequency so as to get the turbulent kinetic energy dissipation rate.

5. The reciprocating ocean microstructure profiler of claim 4, wherein said current meter comprises a current sensing module; said CTD profiler comprises a thermohaline sensing module; said gesture sensor comprises a gesture sensor; and said current sensing module, thermohaline sensing module as well as gesture sensor are connected to the information acquisition ports of the main control module.

6. The reciprocating ocean microstructure profiler of claim 4, wherein said controller is also provided with a buoyancy drive control module, a clock module, a storage module, a PC (personal computer) and a power module; said main module communicates with said clock module, storage module, PC (personal computer) and buoyancy drive control module; said main control module is also connected to the power module and said power module is connected to a battery.

7. The reciprocating ocean microstructure profiler of claim 1, wherein said first drive pump assembly include a motor and a high pressure pump; said high pressure pump is connected to the first oil outlet line in series; said motor is connected to the high pressure pump through a speed reducer driver; said controller is electrically connected to the motor; and said first solenoid valve comprises two circuits connected in parallel, with one circuit being provided with a check valve and the other circuit provided with a flow control valve.

8. The reciprocating ocean microstructure profiler as described in claim 1, wherein the top of said first and second profiler subunits are provided with a brush damper each and said brush damper comprises a plurality of brush blades evenly distributed in a radial pattern.

9. The reciprocating ocean microstructure profiler as described in claim 1, wherein said central stand includes a cylindrical frame in the middle part; both sides of said cylindrical frame are permanently and symmetrically provided with a plurality of support sleeves; said first and second profiler subunits are fixed in the support sleeves at the same side and a plurality of steel cable penetration holes are provided and arranged in the length direction of the cylindrical frame; circumferential pulleys are provided at the upper and lower ends of each steel cable penetration hole and the steel cable passes through the steel cable penetration holes and connected with the circumferential pulleys in a sliding fashion.

10. The reciprocating ocean microstructure profiler as described in claim 1, wherein limit disks are provided in both upper and lower positions; the cable is a steel cable fixed at central holes of the limit disks; and said steel cable is provided with plastic surface.

11. The reciprocating ocean microstructure profiler of claim 10, wherein buffer springs are provided on the bottom of the central stand and used to realize the elastic buffer impact in combination with a lower limit position.

* * * * *